United States Patent [19]  
Gupta et al.

[11] Patent Number: 4,554,291  
[45] Date of Patent: Nov. 19, 1985

[54] IRON/SILICON-BASED CATALYST EXHIBITING HIGH SELECTIVITY TO $C_2$-$C_6$ ALKENES IN CO/$H_2$ FISCHER-TROPSCH REACTIONS

[75] Inventors: Arunava Gupta, Madison; James T. Yardley, Morristown, both of N.J.

[73] Assignee: Allied Corporation, Morris Township, N.J.

[21] Appl. No.: 616,099

[22] Filed: Jun. 1, 1984

Related U.S. Application Data

[62] Division of Ser. No. 494,754, May 16, 1983, Pat. No. 4,468,474.

[51] Int. Cl.$^4$ .................................................. C07C 1/04  
[52] U.S. Cl. ...................................... 518/700; 518/719; 518/720  
[58] Field of Search .................... 518/719, 700, 720

[56] References Cited

FOREIGN PATENT DOCUMENTS 2105604 3/1983 United Kingdom ................ 518/715

OTHER PUBLICATIONS

Haggin, C & En Oct. 26, 1981, pp. 22–24, 26–28, 31–32.

Primary Examiner—Howard T. Mars  
Attorney, Agent, or Firm—Gus T. Hampilos; Gerhard H. Fuchs

[57] ABSTRACT

Finely divided, hydrogen-activated catalyst compositions comprising iron, silicon and carbon or iron and silicon that selectively convert gaseous mixtures of CO and $H_2$, at a temperature of about 150°–450° C. and at pressures of about 10–2000 kPa, into a reaction mixture containing at least about 75% $C_2$-$C_6$ alkenes and no more than about 25% of $CH_4$ and undesirable $CO_2$ by-products are disclosed. A wide range of iron/silicon-based catalyst compositions are conveniently prepared by laser pyrolysis and hydrogen-pretreatment and readily reactivated with hydrogen at elevated temperatures.

6 Claims, No Drawings

IRON/SILICON-BASED CATALYST EXHIBITING HIGH SELECTIVITY TO $C_2$-$C_6$ ALKENES IN CO/$H_2$ FISCHER-TROPSCH REACTIONS

This application is a division, of application Ser. No. 494,754, filed May 16, 1983, now U.S. Pat. No. 4,468,474.

DESCRIPTION

BACKGROUND OF THE INVENTION

This invention relates to hydrogen-activated catalyst compositions comprising iron, silicon and carbon or iron and silicon that provide high catalytic activity and high selectivity to $C_2$-$C_6$ alkenes in CO/$H_2$ Fischer-Tropsch reactions.

Reaction of carbon monoxide and hydrogen mixtures, such as are available from gasification of coal, in the presence of a nickel, cobalt or iron catalyst with a suitable carrier or promoter at a temperature of 150°–450° C. and a pressure of 10–200 kPa atmospheres to produce liquid hydrocarbons is known as the Fischer-Tropsch process. See for example P. Biloen et al., *Advances in Catalysis*, Vol. 30, pp. 165–216 (1981), D. L. King et al., *Catal. Rev. - Sci. Eng.*, Vol. 23, pp. 233–263 (1981) and *Chem. and Eng. News*, Oct. 26, 1981, pp. 22–32.

The Fischer-Tropsch process for production of hydrocarbons from carbon monoxide/hydrogen gas mixtures includes the following reactions:

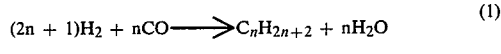  (1)

Alkane Products

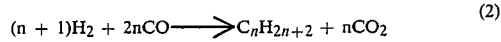  (2)

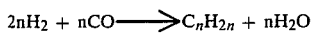  (3)

Alkene Products

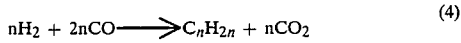  (4)

With many catalysts, water formed in the above reactions is easily converted to carbon dioxide via the water-gas shift reaction:

  (5)

At high temperatures, carbon monoxide is also converted to carbon:

  (6)

  (7)

Even though the Fischer-Tropsch process has been long known and considered as a potentially useful process for manufacture of chemical feedstocks, especially hydrocarbons, unfortunately, most Fischer-Tropsch catalysts materials used to generate hydrocarbons produce a product mixture containing both alkenes and alkanes encompassing a broad range of molecular weights. Reactions of CO/$H_2$ that produce predominately methane (methanation) or carbon dioxide are undesirable. This lack of selectivity makes these prior art Fischer-Tropsch processes uneconomical for large-scale production of hydrocarbons. Improved selectivity is being actively sought by addition to the catalyst, e.g., iron or cobalt of two types of promoters (1) metal oxides, e.g., alumina and (2) energetic promoters, e.g., alkali metal carbonates.

In particular, the improved selectivity for production of light olefins ($C_2$-$C_4$ and $C_2$-$C_6$) is considered highly desirable. In addition, it would be desirable to limit the amounts of $CO_2$ and $H_2O$ produced in reactions 5–7 of the Fischer-Tropsch process. Not only does removal of $CO_2$ require a substantial cost in energy and equipment but $CO_2$ and $H_2O$ also are thought to drastically reduce the service lifetime of the Fischer-Tropsch catalyst.

SUMMARY OF THE INVENTION

In accordance with the present invention, there is provided a process for conversion of CO/$H_2$ into low molecular weight olefin which comprises contacting a gaseous mixture comprising CO and $H_2$ in the ratio of about 3:1 to 1:5 (v/v) with an effective amount of finely divided, hydrogen-activated catalyst composition comprising about 5–15 atom percent Fe about 65–88 atom percent Si and about 2–30 atom percent C or about 10–30 atom percent Fe and about 70–90 atom percent Si, in a reaction zone at a temperature in the range of about 200° C. to about 400° C. and a pressure in the range of about 10 to about 2000 kPa in the absence of externally supplied promoters for a time sufficient to produce a reaction mixture comprising $C_1$-$C_4$ alkanes and $C_2$-$C_6$ alkenes.

In accordance with the present invention, there is also provided a finely divided hydrogen-activated catalyst composition comprising iron, silicon, and carbon and having improved selectivity to $C_2$-$C_6$ alkene products in CO/$H_2$ reactions prepared by a process which comprises contacting, in the gaseous phase, effective amounts of a silicon compound, a hydrocarbon and an organo-iron compound, in a first reaction zone, in the presence of a laser under conditions of laser power absorption, flow rate and pressure sufficient to produce finely divided powder and thereafter contacting said finely divided powder with $H_2$ gas at 400°–500° C. in a second reactor zone for a time sufficient to produce a hydrogen-activated catalyst composition wherein by bulk chemical elemental analysis iron is about 5 to about 15 atom percent, silicon is about 65 to about 88 atom percent, carbon is about 2 to about 30 atom percent.

In accordance with the present invention, there is still further provided a finely divided, hydrogen-activated catalyst comprising iron, silicon and carbon and having a high selectivity to $C_1$-$C_6$ alkenes is CO/$H_2$ reactions, wherein by bulk chemical analysis iron is about 5 to about 15 atom percent, silicon is about 65 to about 88 atom percent, carbon is about 2 to about 30 atom percent and the balance may be oxygen.

DETAILED DESCRIPTION OF THE INVENTION

The present invention provides a finely divided, hydrogen-activated catalyst composition comprising iron, silicon and carbon or iron and silicon, which exhibits moderate catalytic activity for the highly selective conversion of mixtures of carbon monoxide and hydrogen into a reaction mixture containing at least about 75 up to 85% $C_2$-$C_6$ alkenes and low amounts of the undesirable $CO_2$ by-product, compared to prior art catalysts. See, for example, Tables III a+b, hereinbelow for a summary of results for a preferred embodiment of the present invention. Moreover, the catalysts of the present invention maintained their catalytic activity and high selectivity over relatively long periods of time. Regeneration of partially deactivated catalyst may be accomplished readily by treatment with hydrogen at elevated temperatures, e.g., 450°–550° C.

The high selectivity to $C_2$–$C_6$ alkenes, low amounts of alkanes (less than about 25% of total hydrocarbon products were $C_1$–$C_4$ alkanes of which methane is the predominate component) and $CO_2$ is particularly surprising for the iron-based catalyst composition of the present invention in view of the teachings of the prior art wherein inhibitors or promoters or active supports were included in iron-based catalyst systems to suppress formation of alkanes.

The process for conversion of mixtures of gaseous carbon monoxide and hydrogen in the presence of an effective amount of the catalyst compositions of the present invention is conveniently conducted at a temperature in the range of about 150° to about 450° C., normally 250°–350° C., a pressure in the range of about 10 to about 2000 kPa, normally 100–1000 kPa, in a batch or flow reactor system. The volume ratio of carbon monoxide to hydrogen is conveniently in the range of about 3 to 1 to about 1 to 5 and normally is about 1 to 2–3.

The process of the present invention is conducted for a time sufficient to form a reaction mixture, containing methane, $C_2$–$C_6$ alkenes and alkanes, carbon dioxide, water and less than 0.5% alcohols and ethers. The reaction mixture may be entrapped in a suitable trapping means such as a condenser and thereafter separated by standard techniques, e.g. gas chromatography.

The activity of the catalyst compositions of the present invention is increased at temperatures of about 350°–450° C. However, the product distribution shifted toward lower molecular weight hydrocarbons with substantially higher amounts of methane and carbon dioxide. Furthermore, the catalyst deactivates faster at temperatures of about 350°–450° C. The activity of the catalyst is decreased at temperatures of about 200°–250° C. and the product distribution was broadened with formation of significant amounts of hydrocarbons higher than $C_6$. Temperatures in the range of about 250° C.–350° C. were preferred for maximizing catalytic activity, service lifetime and selectivity to $C_2$–$C_6$ alkenes.

The process of the present invention may be operated in batch or continuous mode. In the examples provided hereinbelow an unstirred batch reactor was employed. It is believed that a continuous flow reactor would minimize secondary reactions of initially formed products and extend the service lifetime of the catalyst.

The reactor design may be of any convenient design, such as disclosed in *Chem. and Eng. News*, Oct. 26, 1981 at pp. 26–31. A slurry reactor system may be especially convenient for the ultra finely divided catalyst compositions of the present invention.

The catalyst composition of the present invention were prepared by pretreatment of the finely divided powders of iron, silicon and carbon or iron and silicon with hydrogen at temperatures in the range of about 450° C. to about 550° C. for at least about 1 hour in a first reaction zone which may conveniently be the same reaction zone used for the conversion of gaseous carbon monoxide and hydrogen into hydrocarbons, especially $C_2$–$C_6$ alkenes. Finely divided powders not pretreated with hydrogen were not catalytically active in $CO/H_2$ conversions. The catalytic activity of the catalyst composition of the present invention gradually decreases with the time to about one-half the initial activity and appeared reasonably stable under repeated exposure to mixtures of carbon monoxide and hydrogen in accordance with process of present invention. Should the catalyst of the present invention become partially or even completely deactivated, the catalyst may be reactivated by treatment with hydrogen gas at 450°–550° C. for a time sufficient to produce a hydrogen-activated catalyst having high selectivity to $C_2$–$C_6$ alkenes. The volatile products produced by pretreatment or reactivation with hydrogen comprised methane, ethane and water. By transmission electron microscopy and electron diffraction analysis, the morphology and crystalline character of the finely divided catalyst particles before and after heat treatment with hydrogen at about 450° C.–550° C. remained substantially unchanged; however, after heat treatment (1 hr at 450° C.) of a catalyst composition of the present invention, the average diameter of the particles increased slightly, normally from about 14 nm to about 20 nm.

The catalyst compositions useful in the present invention comprise about 5 to about 15 atom percent iron, about 65 to about 88 atom percent silicon and about 2 to about 30 atom percent carbon or about 10 to about 30 atom percent iron and about 70 to about 90 atom percent silicon. The preferred catalyst composition comprises iron, silicon and carbon.

The iron/silicon/carbon catalyst compositions of the present invention were conveniently prepared by contacting, in the gaseous phase, effective amounts of a silicon compound, a hydrocarbon and an organo-iron compound, in a reaction zone, in the presence of a laser under conditions of laser power absorption, flow rate and pressure for a time sufficient to produce finely divided powder; for preparation of the iron/silicon catalyst compositions, the hydrocarbon reactant would not be included. The finely divided powders were thereafter treated with hydrogen at 450° –550° C. for a time sufficient to produce the active catalyst compositions of the present invention.

The reactants useful in the preparation of the catalyst compositions of the present invention conveniently are gases at pressures of 10–100 kPa or have a vapor pressure of at least about 5 torr at ambient temperature. At least one of the reactants must absorb radiation emitted by the laser.

Any source of gaseous carbon monoxide and hydrogen, such as gasified coal or synthesis gas may be used in the process of the present invention.

Among the silicon compounds found useful in the present invention are those having the formula $SiH_{4-r}X_r$ and $Si_pH_{2p+2}$ wherein r is 0, 1 or 2 and wherein X is F or Cl and wherein p is 1–6. Exemplary silicon compounds are $SiH_4$, $SiH_2Cl_2$, $SiH_2F_2$, $SiH_3Cl$, $SiH_3F$, $Si_2H_6$, $Si_3H_8$. $SiH_4$ is preferred.

Among the hydrocarbons found useful in the present invention are those having the formulae $C_mH_{2m-2}$, $C_xH_{2x}$ and $C_nH_{2n+2}$ wherein m is 1–4, x is 2–10 and n is 1–10. Exemplary hydrocarbons are $C_2$–$C_8$ alkynes, such as ethyne, propyne, $C_2$–$C_8$ alkenes such as ethene, propene, isomeric butenes and pentenes, and $C_1$–$C_{10}$ alkanes such as methane, ethane, propane, isomeric butanes and pentanes. Ethene and ethyne are preferred hydrocarbons.

Among the organo-iron compounds found useful in the present invention are iron carbonyls especially $Fe(CO)_5$, iron acetylacetonate and ferrocene $(Fe(C_5H_5)_2)$.

The type of laser used in the present invention is not critical. A continuous wave $CO_2$ laser with intensities in the range of $10^4$-$10^6$ watts/cm$^2$ is especially useful.

By the term "finely divided" particles as used herein to describe the catalyst composition or the present invention is meant particles having a size in the range of about 6 to about 60 nm. The catalyst composition of the present invention normally have a BET surface area of about 100-150 m$^2$/g and a spherical shape with a substantially uniform diameter of about 10 to about 20 nm by transmission electron microscopy.

By elemental analysis, the catalyst compositions of the present invention may contain no more than about 1.5 to 2.0% by weight oxygen and trace amounts of metals. The trace amounts of P, Cl and K are thought to be artifacts from the analysis.

The catalyst composition comprising iron, silicon and carbon was analyzed by X-ray diffraction (CuK$\alpha$ radiation) and electron diffraction and found to contain polycrystalline FeSi$_2$ and possibly elemental crystalline silicon and a crystalline carbide, which could be iron and-/or silicon carbide. In addition x-ray photoelectron spectroscopic analysis of the iron/silicon/carbon catalyst composition showed carbide-type carbon, possibly silicon carbide to be present. While the precise structure of the iron/silicon/carbon catalyst is not known, the iron/silicon/carbon are combined in some form more chemically intimate than a simple physical mixture.

For example, a physical mixture of FeSi$_2$ and SiC (both prepared by the same $CO_2$ laser pyrolysis procedure used for making the catalyst compositions of the present invention) was tried as a catalyst for conversion of gaseous carbon monoxide and hydrogen, and found to be catalytically uninteresting, i.e., had lower activity than pure FeSi$_2$ showed in the process of the present invention, under similar conditions.

EXPERIMENTAL

EXAMPLE 1

Preparation of Catalysts

The catalyst materials were prepared using a laser pyrolysis technique in a reaction chamber similar to that described in "Sinterable Powders from Laser-Driven Reactions" by J. S. Haggerty et al. in *Laser-Induced Chemical Processes* (Plenum Press, New York, 1981) at pages 165-241. A 50 watt CW $CO_2$ laser was passed into the reaction chamber through a NaCl window and was arrested with a water-cooled copper block. The laser was focused down to a 2 mm spot using a 25.4 cm focal length NaCl lens.

The reactant gases used were silane (Matheson, semiconductor purity), ethylene (Matheson, 99.5%), iron pentacarbonyl (Alfa, 99.5%) and argon (MG Scientific, prepurified grade). The iron pentacarbonyl liquid was placed in a glass bubbler and argon gas was used to carry the iron carbonyl vapor to the reaction chamber. The reactant gases entered the chamber, orthogonal to the laser beam, through a 16 mm stainless steel nozzle, 5-7 mm below the laser below. The flow rates of all the reactants were independently controlled using flow meters. The flowing mixture was pyrolyzed using the focused 50 watt CW $CO_2$ laser. Table I lists the various process parameters used in several different runs. The $CO_2$ laser radiation at 10.6$\mu$ (P20 line) was primarily absorbed by silane gas and to some extent by ethylene. Iron pentacarbonyl has no absorption at this wavelength. A reaction flame was usually visible with the formation of the particles. Under certain flow conditions, however, plume formation was observed without any accompanying flame. A typical run lasted for 2-3 hours and resulted in formation of 2-3 grams of the powder.

A coaxial argon steam is used to collect the particles in a microfibre filter (Balstron, Inc.; grade AAQ). The results are summarized in Table I. The bulk chemical analyses for catalyst are given in Table II.

EXAMPLE 2

Pretreatment of Catalysts

The materials prepared in accordance with the procedure of Example 1 were pretreated in $H_2$ before use as catalysts for the $H_2$/CO reaction. Typically, 8-10 mg of the sample was placed in a 5 mL glass reactor and filled with 740 torr of $H_2$. The sealed reactor was then placed in a clam-shell oven (Lindberg Model M-1006-S) and heated to temperatures of 450°-550° C. for varying lengths of time (1-16 hrs). Most pretreatments were done at 450° C. for 2 hrs. A quartz reactor was used for temperatures higher than 450° C. The gas recovered from pretreatment was injected into a Hewlett-Packard Model 5880 gas chromatograph (equipped with a 6'×¼" glass Chromosorb 102 column and flame ionization detector) to analyze for any products formed.

EXAMPLE 3

Experimental Procedure for Fischer-Tropsch Reactor

After pretreatment in hydrogen, the reactor of Example 2 was evacuated and filled with a feed gas mixture of $H_2$ and CO (premixed gas supplied by Matheson) at room temperature and 740 torr. The feed gas was passed through a coil cooled to liquid nitrogen temperature to remove Fe(CO)$_5$ contamination. $H_2$/CO ratios of 1:2, 1:1 and 3:1 were used in these experiments. The sealed reactor was placed in a temperature controlled clam-shell oven which had been preheated to the reaction temperature. The reaction was carried out at temperatures ranging from 250°-350° C. for 1 hr-16 hr periods. After reaction, the gas mixture from the reactor was injected into the Model 5880 gas chromatograph for analysis of hydrocarbons up to C$_6$. Only C$_2$ and C$_3$ alkenes and alkanes were well resolved; the higher hydrocarbons were either partially resolved (C$_4$'s) or not resolved at all (C$_5$'s and C$_6$'s). Carbon mass balance in all experiments showed that the conversion of carbon monoxide can, with a few percent, be accounted for by formation of C$_1$-C$_6$ hydrocarbons and carbon dioxide. The gas mixture was also injected into another gas chromatograph (Hewlett-Packard Model 5710A) equipped with a thermal conductivity detector for analysis of CO and $CO_2$. Both chromatographs were calibrated with standards of the gases involved. The results for conversion of CO/$H_2$ using a preferred (hydrogen-activated catalyst (run #2 of Table II) are summarized in Table III.

TABLE I

| | Process Parameters for Laser Synthesis of Fe/Si and Fe/Si/C Catalyst Powders[1] | | | | |
|---|---|---|---|---|---|
| Run # | $P_c$[2] (Torr) | Flow Rates[3] | | | $p$[7,8] |
| | | SiH$_4$[4] | C$_2$H$_4$[5] | Ar[6] | Fe(CO)$_5$ |
| 1 | 204-213 | 40 | 0 | 18 | 32 |
| 2 | 270-275 | 47 | 20 | 19 | 22 |
| 3 | 206-220 | 40 | 0 | 18 | 27 |
| 4 | 260-280 | 45 | 20 | 18 | 27 |
| 5 | 270-280 | 45 | 20 | 18 | 32 |

TABLE I-continued

Process Parameters for Laser Synthesis
of Fe/Si and Fe/Si/C Catalyst Powders[1]

| Run # | $P_c$[2] (Torr) | Flow Rates[3] SiH$_4$[4] | C$_2$H$_4$[5] | Ar[6] | p[7,8] Fe(CO)$_5$ |
|---|---|---|---|---|---|
| 6 | 260–280 | 45 | 20 | 19 | 30 |
| 7 | 220–225 | 40 | 0 | 18 | 28 |

Footnotes

[1] $CO_2$ Laser Intensity = 1400 W/cm$^2$

[2] Cell pressure

[3,4] The flow meters were not calibrated for the different gases. The numbers quoted denote the position of the glass ball in Matheson Models 600, 602, 604 flow meters the positions of ball in Matheson Model 600 flow meter for SiH$_4$ were 40–47; the equivalent flow rate for air was 10–12 cm/min.

[5] Positions of glass ball in Matheson Model 602 flow meter; the equivalent flow rate for air was 25 mL/min.

[6] Position of glass ball in Matheson Model 604 flow meter; the equivalent flow rate for air is 1000 mL/min.

[7] Vapor pressure of Fe(CO)$_5$ was calculated using the equation: log P (torr) = −(2096.7° K./T) + 8.4959.

[8] Argon flow rate (the position of glass ball in Matheson Model 602 flow meter) was 30 for Runs 1–5, 15 (Run #6) and 20 (Run #7). The equivalent flow rate for air was 45 mL/min. The pressure of Argon was 1 atm.

TABLE II

Wet Chemical Analysis for Fe/Si and Fe/Si/C Catalyst Powders of Table I

| Run # | Composition wgt % (atom %)[2,3] Fe | Si | C | Total[1] |
|---|---|---|---|---|
| 1 | 33.8 (20.7) | 65.0 (79.3) | — | 98.8 |
| 2 | 20.5 (10.6) | 70.8 (72.1) | 7.21 (17.1) | 98.5 |
| 3 | 23.9 (13.6) | 74.1 (83.9) | 0.94 (2.4) | 98.9 |
| 4 | 17.7 (9.0) | 75.0 (75.7) | 6.46 (15.3) | 99.2 |
| 5 | 22.4 (11.8) | 70.0 (73.3) | 6.08 (14.9) | 98.5 |
| 6 | 11.6 (5.8) | 79.8 (79.9) | 7.12 (16.3) | 98.5 |
| 7 | 19.2 (10.5) | 79.3 (86.3) | 1.25 (3.2) | 99.9 |

Footnotes

[1] Balance might be oxygen but no oxygen analysis was performed

[2] Atom %

[3] AA Spectroscopic Analyses (Run #2) showed: 0.01% Al; 0.01% Ca; 0.05% Cr; 0.01% Cu; Fe(Major); 0.05% Ni; 0.01% Mg; Si(Major) and 0.02 Ti (all Max., and all % by weight)

TABLE IIIa

Selectivity of Fe/Si/C Catalyst of Run #2
of Table II in Fischer-Tropsch Synthesis[a]

| Run # | H$_2$/CO | Percent Product Distribution[d] C$_1$ | C$_2$ | C$_3$ | C$_4$ | C$_5$ | C$_6$ |
|---|---|---|---|---|---|---|---|
| 8 | 1:2 | 16.5 | 20.6 | 24.7 | 17.0 | 12.1 | 8.7 |
| 9 | 1:2 | 16.6 | 21.6 | 25.6 | 16.7 | 11.4 | 7.8 |
| 10 | 1:2 | 13.3 | 20.2 | 27.5 | 17.6 | 12.0 | 9.3 |
| 11 | 1:1 | 24.0 | 23.5 | 23.9 | 13.9 | 8.8 | 5.7 |
| 12 | 1:1 | 18.1 | 20.8 | 26.3 | 16.3 | 10.8 | 7.5 |
| 13 | 3:1 | 22.7 | 19.0 | 23.6 | 15.9 | 10.9 | 7.8 |
| 14 | 3:1 | 23.0 | 19.2 | 24.0 | 16.0 | 10.7 | 6.9 |

TABLE IIIb

Selectivity of Fe/Si/C Catalyst of Run #2
of Table II in Fischer-Tropsch Synthesis[a]

| Run # | % CO Conv[b] | % CO$_2$ of by-products[c] | % C$_2$–C$_4$ alkenes of HC[d] | % C$_2$–C$_4$ alkanes of HC[d] | % C$_2$–C$_6$ alkenes of HC[d] |
|---|---|---|---|---|---|
| 8 | 3.1 | 20.5 | 60.3 | 2.0 | 83.5 |
| 9 | 6.2 | 32.0 | 60.7 | 3.2 | 83.4 |
| 10 | 38.5 | 97.0 | 59.0 | 6.3 | 86.7 |
| 11 | 4.4 | 17.3 | 57.8 | 3.5 | 76.0 |
| 12 | 47.5 | —[e] | 54.8 | 8.7 | 81.9 |
| 13 | 25.5 | 10.6 | 53.6 | 4.9 | 77.3 |
| 14 | 39.2 | 14.0 | 52.1 | 7.1 | 77.0 |

[a] Temp: 300° C.; Pressure: 740 torr

[b] The % CO conversion has been calculated from reaction stoichiometry, and the actual amounts of hydrocarbons and CO$_2$ produced in the reaction

[c] This is the ratio of actual amount of CO$_2$ produced to amount of CO$_2$ expected for stoichiometric formation of CO$_2$. The amount of water formed as a by-product is: 100 - % CO$_2$

[d] Hydrocarbons higher than C$_6$, which constitute less than 5% of the product, have been neglected.

[e] Not measured

We claim:

1. A process for conversion of CO/H$_2$ into low molecular weight olefins which comprises contacting a gaseous mixture comprising CO and H$_2$ in the ratio of about 3:1 to 1:5 (v/v) with an effective amount of a finely divided, hydrogen-activated catalyst composition comprising about 5–15 atom percent Fe, about 65–68 atom percent Si, and about 2–30 atom percent C in a reaction zone at a temperature in the range of about 150° C. to about 450° C. and a pressure in the range of about 10 to about 2000 kPa for a time sufficient to produce a reaction mixture comprising C$_2$–C$_6$ alkenes, said hydrogen-activated catalyst having been prepared by a process which comprises contacting effective amounts, in the gaseous phase, of a silicon compound, a hydrocarbon and an organo-iron compound under conditions to produce a product and thereafter contacting the product with H$_2$ gas at a temperature between about 450° C. and about 550° C. for a time sufficient to produce the hydrogen activated catalyst composition.

2. The process of claim 2 wherein the catalyst composition has a bulk elemental analysis wherein iron is about 10 atom percent, silicon is about 72 atom percent, and carbon is about 17 atom percent and wherein the hydrogen-activated catalyst composition comprises polycrystalline FeSi$_2$.

3. The process of claim 1 wherein the gaseous mixture comprises about one volume of CO and about 2–3 volumes of H$_2$ and wherein the pressures are about 100 to about 1000 kPa and wherein the temperature is about 250°–350° C.

4. The process of claim 1 wherein the reaction zone is a slurry-type reactor.

5. A process for converting CO/H$_2$ into low molecular weight olefins which comprises contacting a gaseous mixture comprising CO and H$_2$ in a ratio of about 3:1 to 1:5 (v/v) with an effective amount of a finely divided, hydrogen-activated catalyst composition comprising about 5–15 atom percent Fe, about 65–68 atom percent Si, and about 2–30 atom percent C in a reaction zone at a temperature in the range of about 150° C. to about 450° C. and a pressure in the range of about 10 to about 2000 kPa in the absence of externally supplied promotors for a time sufficient to convert said CO and H$_2$ into a reaction mixture comprising at least about 75% C$_2$–C$_6$ alkenes.

6. The process of claim 5 wherein the reaction mixture further comprises up to about 25% C$_1$–C$_4$ alkanes.

* * * * *